United States Patent

Yamamoto et al.

[11] Patent Number: 5,902,274
[45] Date of Patent: May 11, 1999

[54] CATHETER ASSEMBLY

[75] Inventors: Hideki Yamamoto; Masaya Nakashima, both of Osaka, Japan

[73] Assignee: Nissho Corporation, Osaka, Japan

[21] Appl. No.: 08/905,024

[22] Filed: Aug. 1, 1997

[30] Foreign Application Priority Data

Aug. 2, 1996 [JP] Japan ................................. 8-204419

[51] Int. Cl.⁶ ................................................. A61M 5/00
[52] U.S. Cl. ........................... 604/164; 604/177; 604/280
[58] Field of Search .................................... 604/164, 165, 604/166, 174, 177, 158, 280, 264, 50, 51, 49, 198, 263

[56] References Cited

U.S. PATENT DOCUMENTS

| | | | |
|---|---|---|---|
| 4,840,613 | 6/1989 | Balbierz | 604/51 |
| 4,982,760 | 1/1991 | Mustaklem | 137/559 |
| 5,195,974 | 3/1993 | Hardy | 604/110 |
| 5,409,461 | 4/1995 | Steinman | 604/164 X |
| 5,542,930 | 8/1996 | Schur | 604/164 |
| 5,688,249 | 11/1997 | Chang et al. | 604/164 X |
| 5,697,914 | 12/1997 | Brimhall | 604/177 |

FOREIGN PATENT DOCUMENTS

| | | |
|---|---|---|
| 1 025 223 | 2/1958 | Germany . |
| 976 852 | 12/1964 | United Kingdom . |

*Primary Examiner*—John D. Yasko
*Attorney, Agent, or Firm*—Kubovcik & Kubovcik

[57] ABSTRACT

A catheter assembly includes a catheter 1 having a catheter hub 11 provided at proximal end thereof, a wing member 2 supporting the catheter 1, a tubular member 3 which is fixed to the wing member 2 and into which the catheter is slidably inserted, a sheath 4 slidably covering around the tubular member 3 and the catheter 1 and fixed to the catheter hub 11 coaxially with the catheter 1, and a piercing member 5 comprising a piercing needle 51 provided at distal end thereof, a wire 52 and a wire hub 53, where the piercing member 5 is slidably inserted into the catheter 1 such that the distal end of the piercing needle 5 is disposed to extend beyond the distal end of the catheter 1. A long accommodating tube 6 for accommodating a piercing member therein may be provided between the catheter hub 11 and the wire hub 53.

13 Claims, 8 Drawing Sheets

CATHETER ASSEMBLY

BACKGROUND OF THE INVENTION

1. Field of the Invention

The present invention relates to a catheter assembly capable of sanitarily and safely inserting a catheter into a desired position in a human body.

2. Description of Related Art

A catheter assembly is used for introducing a cannula made of a synthetic resin into veins, arteries or a coelom of a patient and injecting a liquid medicine or removing a fluid. When a catheter is inserted into, for example, a vein, there has been conventionally used a method where a piercing needle having an inner diameter larger than an outer diameter of a catheter is first pierced into a vein. A catheter is then guided to a desired position of the vein through a bore (lumen) of the piercing needle and, thereafter, only the catheter is left in the vein by removing the piercing needle from the vein. With this method there is a fear that blood will leak from the skin surface when the piercing needle is removed from the vein or that bacteria will invade the vein or the like when the piercing needle is removed from the vein. Accordingly, the insertion operation of the catheter must be carried out under an aseptic condition.

Therefore, there has been proposed a catheter assembly capable of aseptically inserting a catheter into a human body by guiding the catheter using a sheath without touching the catheter (Japanese Unexamined Patent Publication No. JP-A-2-13471, Japanese Unexamined Patent Publication No. JP-A-2-111376).

The catheter assembly according to Japanese Unexamined Patent Publication No. JP-A-2-13471, is comprised of a cannula, an inserter for slidably holding the cannula and a hub structure attached to a proximal end of the cannula, and is characterized in that a sheath is attached to the hub structure and surrounds the cannula, and the inserter is provided with a sheath stripping means and sheath locking members. After a distal end of the catheter is inserted into a human body along with a needle and the needle is removed from the catheter, the cannula can be inserted further into the body by pulling a tab of the sheath projecting at a distal end thereof. The cannula integrated with the sheath by the hub structure is prevented from retracting by sheath locking members.

Meanwhile, the catheter assembly according to Japanese Unexamined Patent Publication No. JP-A-2-111376, is comprised of a cannula, an inserter for slidably holding the cannula and a hub structure attached to a proximal end of the cannula, and characterized in that a long accommodating tube for accommodating a needle (long piercing member) is provided therein. After a distal end of the catheter is inserted into a human body along with the needle and the needle is removed from the catheter, the needle contaminated with blood can be accommodated in the long accommodating tube.

However, with the a catheter assembly disclosed in Japanese Unexamined Patent Publication No. JP-A-2-13471, there is a danger of exposing the catheter to the outer atmosphere immediately in front of the sheath stripping means when stripping the sheath from the catheter, and insertion failure or breakage of catheter may be caused because the stripping resistance of the sheath from the catheter is large. Further, erroneous insertion may be caused since the resistance in inserting the catheter into a blood vessel is difficult to be perceived by an operator since the stripping resistance of the sheath from the catheter is large. Further, a manipulatively familiar conventional method in which a catheter is inserted into a blood vessel by pushing it is preferably used if safety in inserting the catheter is regarded as important. However, according to the above-described catheter assembly, although the catheter can be inserted into a blood vessel by pushing it if the rigidity of the sheath is increased, the stripping resistance of the sheath is also increased. On the other hand when the rigidity of the sheath is weakened, the sheath cannot be inserted by pushing it since kinking or bending is caused in the sheath.

Meanwhile, according to the catheter assembly of Japanese Unexamined Patent Publication No. JP-A-2-111376, although the needle can be accommodated in the long accommodating tube, if blood is adhered to a wire, the operator can touch the wire with his hand and, accordingly, the danger of blood borne infections still remains.

The present invention has been developed in view of the above-described situation and it is an object of the present invention to provide a catheter assembly capable of sanitarily and safely inserting a catheter into a desired position in a human body by pushing it. Further, it is an object of the present invention to provide a catheter assembly capable of safely disposing of a piercing needle which has been removed after inserting a catheter.

SUMMARY OF THE INVENTION

The inventors have found, as a result of an intensive study, that the problem of kinking or bending of a catheter is resolved by covering a periphery of a tubular member in which the catheter is inserted with the sheath that is provided around the catheter.

Further, the inventors have found that the problem of blood contamination is resolved by providing a catheter assembly with a long accommodating tube capable of accommodating not only a piercing needle but also a wire.

According to the present invention, the catheter assembly includes a catheter, a wing member, a tubular member, a sheath, a wire, a wire hub and a piercing member, the catheter having a lumen extending from a proximal end to a distal end and a hub provided at the proximal end thereof. The wing member has a support channel for slidably accommodating and supporting the catheter. The tubular member is fixed to a proximal end of the support channel of the wing member and the catheter is slidably inserted therein. The sheath has a slit or a weakened portion extending in a longitudinal direction from a distal end to a proximal end and is fixed to the hub coaxially with the catheter. The sheath slidably covers around the catheter and a periphery of the tubular member. The piercing member includes a piercing needle provided at a distal end of the catheter, a wire whose distal end is connected to a proximal end of the piercing needle and which extends beyond the hub, and a wire hub fixed to a proximal end of the wire. The piercing member is slidably inserted through the lumen of the catheter and the distal end thereof is disposed to extend beyond the distal end of the catheter.

Here, a sheath stripping member can be provided contiguously to the proximal end of the support channel and on the periphery of the tubular member. The sheath stripping member is constituted such that the outer diameter gradually increases toward the distal end and the distal end thereof is larger than the inner diameter of the sheath. Further, an adjusting means for adjusting the direction of an edge face and the lie distance of the piercing needle may be provided to the wire hub. Also, a long accommodating tube for accommodating the piercing member therein may be provided between the hub of the catheter and the wire hub coaxially with the wire. The long accommodating tube is preferably comprised of a connection member whose distal end is connectable to the catheter hub, a soft sleeve whose distal end is connected to a proximal end of the connection member and a sleeve protecting cylinder capable of accommodating the sleeve. A proximal end of the sleeve is preferably connected to the wire hub and the sleeve protecting cylinder is preferably connectable to the catheter hub and the wire hub. The long accommodating tube may include a wire disinfecting member provided around the wire.

DETAILED DESCRIPTION OF THE PREFERRED EMBODIMENTS

Embodiments of the present invention are explained below with reference to the drawings.

Figure 1:
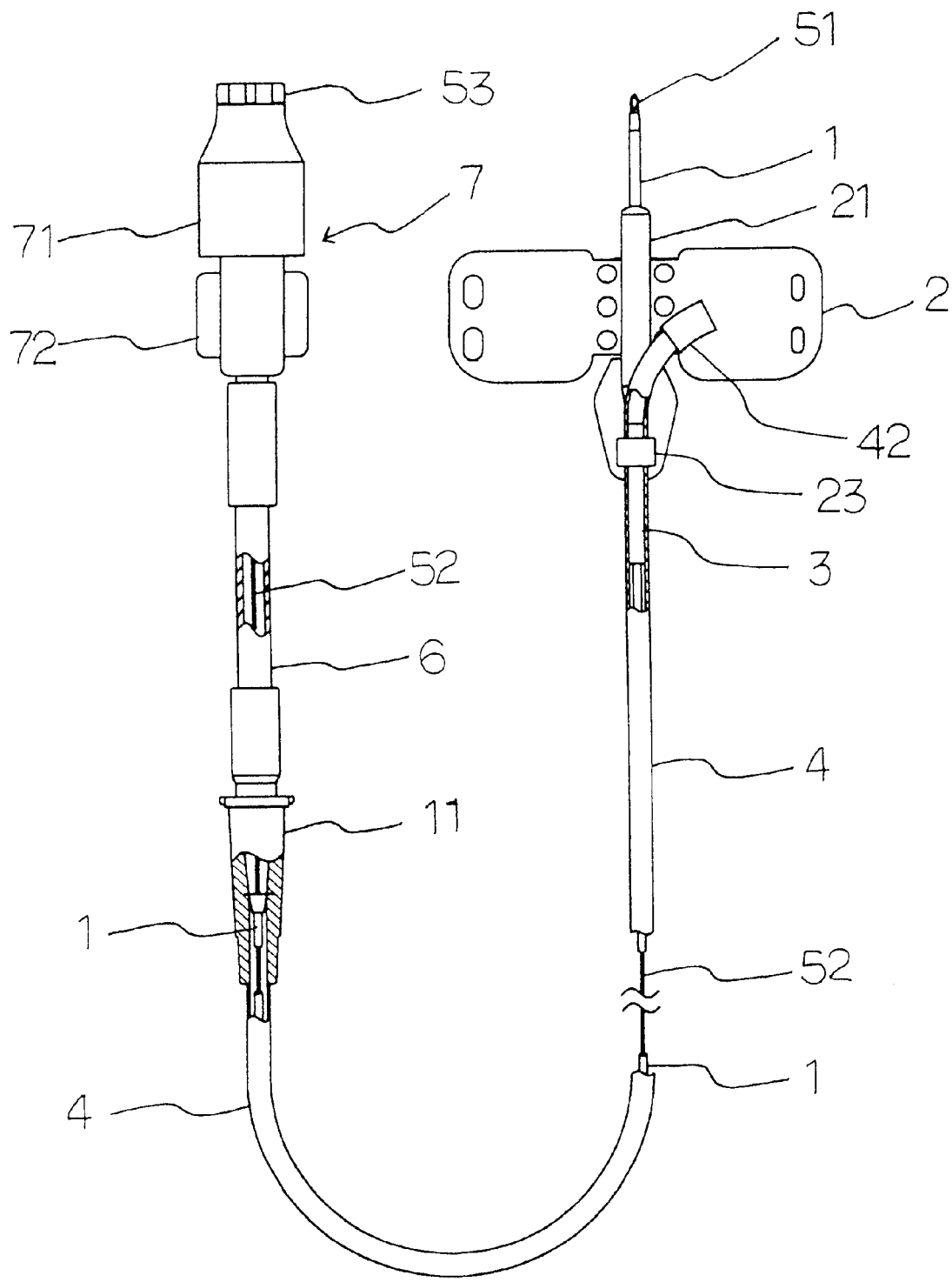
FIG. 1 is a partially sectioned plane view of a catheter assembly showing an embodiment of the present invention.

As shown in FIG. 1, a catheter assembly of the present invention includes a catheter 1 having a catheter hub 11 at a proximal end thereof, a wing member 2 for supporting the catheter 1, a tubular member 3 fixed to the wing member 2 and having catheter 1 slidably inserted therein, a sheath 4 slidably covering a periphery of the tubular member 3 and the catheter 1 and fixed to the catheter hub 11 coaxially with the catheter 1, and a piercing member 5 comprised of a piercing needle 51 provided at a distal end thereof, a wire 52 and a wire hub 53. The piercing member 5 is slidably inserted in the catheter 1 and a distal end thereof is disposed to extend beyond a distal end of the catheter 1. Further, preferably, a long accommodating tube 6 is provided between the catheter hub 11 and the wire hub 53.

Figure 3:
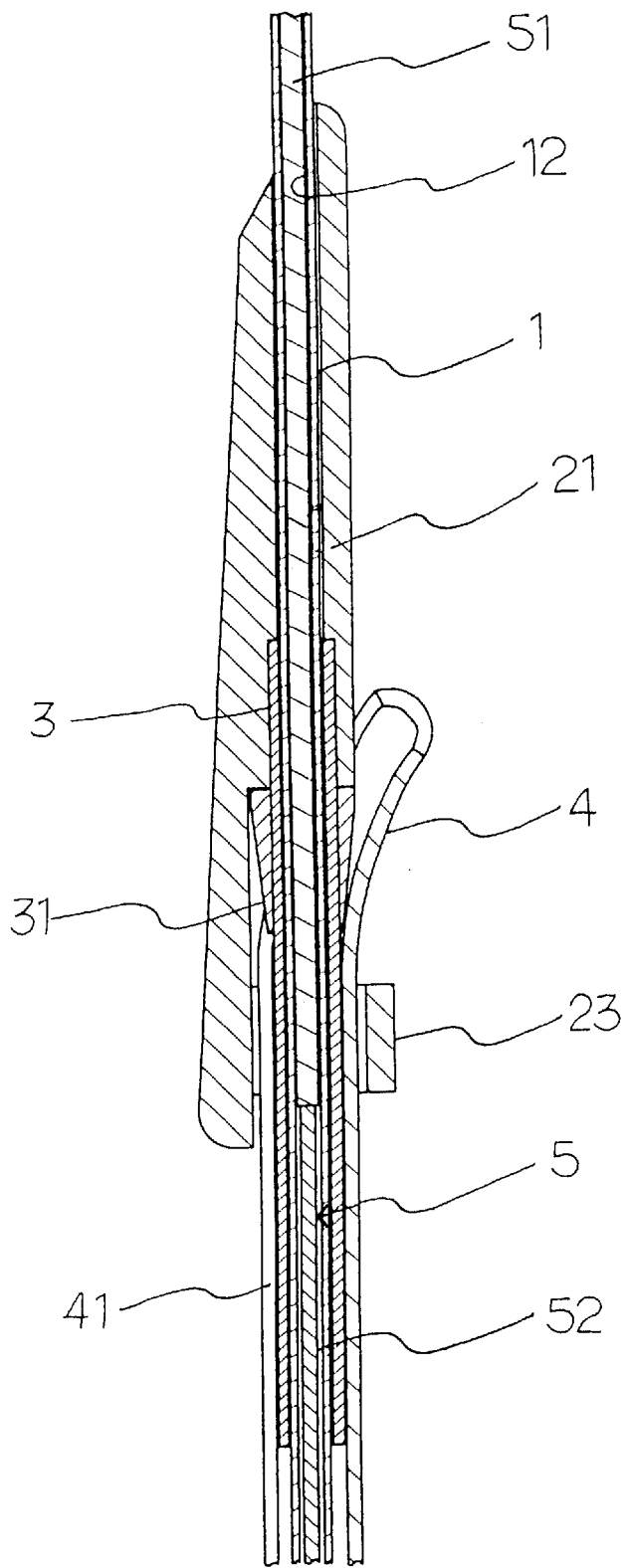
FIG. 3 is an enlarged sectional view taken along a line 3—3 in respect of the essential portions of FIG. 2.

The catheter 1 has a proximal end and a distal end, and is attached to catheter hub 11 at the proximal end thereof. The catheter 1 has a lumen 12 extending from the proximal end to the distal end. The piercing needle 51 and the wire 52 of the piercing member 5 are inserted into said lumen 12 as shown in FIG. 3. Although the catheter of the present invention may be made of any material so far as the material is suitable for introducing into an organism, polyfluoroethylene-polypropylene, polyurethane or the like is preferably adopted. The material of the catheter may include a radiopaque agent or a drug such as an antithrombotic agent, an antibiotic agent and an anticoagulant agent or the like.

Figure 2:
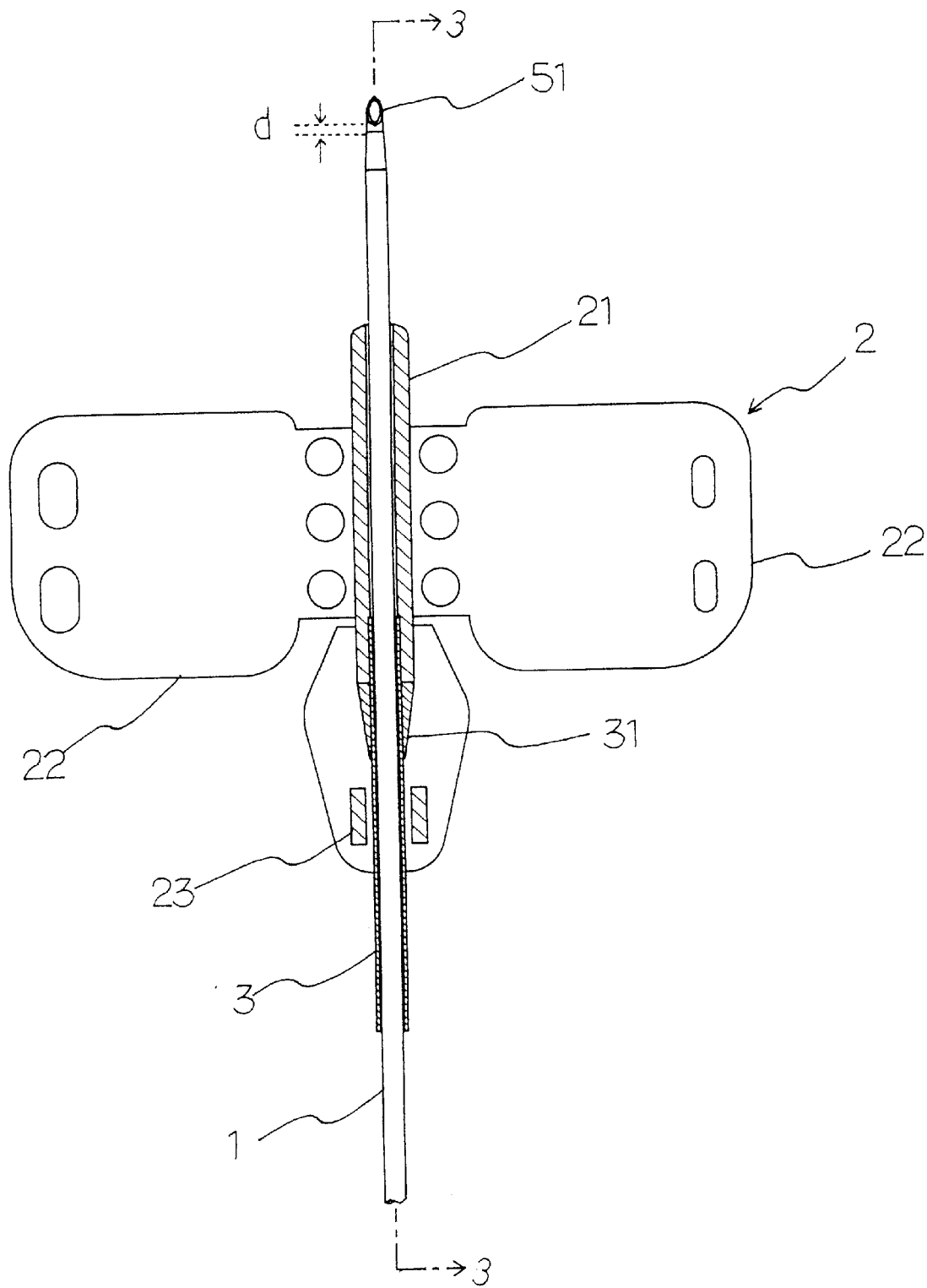
FIG. 2 is a plane view enlarging sections of a portion of FIG. 1 including a wing member.

The catheter 1 is inserted in a support channel 21 of the wing member 2. As shown in FIG. 2 and FIG. 3, the wing member 2 is composed of the support channel 21 shaped like a tube for slidably accommodating and supporting the catheter 1 therein, a pair of wings 22 symmetrically provided about the support channel 21 and a sheath holding means 23 preferably provided on the proximal end side of the support channel 21 and approximately at the midpoint of the tubular member 3. Although the sheath holding means 23 is not always necessary, if a slit 41 in the longitudinal direction is formed in the sheath 4, the sheath holding means 23 prevents the slit 41 of the sheath 4 from opening before the sheath is separated from the catheter 1. If a tab 42 is provided at the distal end of the sheath 4, when the sheath 4 is pulled toward the proximal end side, the tab 42 is caught by the sheath holding means 23 whereby the sheath 4 can be prevented from slipping off the support channel 21 and the tubular member 3. Incidentally, as shown in FIG. 3, the proximal end side of the support channel 21 is preferably inclined with respect to the skin such that it is easy for the piercing needle to pierce the skin. The angle of inclination of the distal end side of the support channel (measured with respect to the axis of the support channel) is normally between 15° and 45°.

The tubular member 3 is fixed to the proximal end portion of the support channel 21 of the wing member 2. As shown in FIG. 2 and FIG. 3, the catheter 1 is slidably inserted in the tubular member 3 and the sheath 4 covers the tubular member 3. The tubular member 3 is generally made of a metal or hard synthetic resin. The outer sheath 4 is separated from the inner catheter 1 at the tubular member 3 and then covers the tubular member 3. When the sheath 4 is pushed along the tubular member 3, the sheath 4 is stripped from the tubular member 3 after the tubular member 3 separates the sheath 4 from the catheter 1. Therefore, in the stripping operation the catheter 1 can be prevented from being exposed and the stripping resistance of the sheath 4 does not directly act on the catheter 1. A sheath stripping member 31, may be provided contiguously to the proximal end of the support channel 21 and on a periphery of the tubular member 3. The sheath stripping member 31 is constituted such that an outer diameter thereof gradually increases and an outer diameter of the distal end thereof becomes larger than an inner diameter of the sheath 4. The outer diameter of the sheath stripping member 31 may have a size such that the sheath 4 can be split along the slit 41 or a weakened portion (not illustrated).

The sheath 4 is a tubular member having the slit 41 or a weakened portion in the longitudinal direction from the distal end to the proximal end, and the catheter 1 is slidably inserted therein. The proximal end of the sheath 4 is fixed to the catheter hub 11 coaxially with the catheter 1. Further, the distal end portion of the sheath 4 slidably covers the tubular member 3 and is separated from the catheter 1 inserted in the sheath 4 at the proximal end of the tubular member 3. Although the material for making the sheath 4 is not particularly limited as long as it is a soft material, generally, polyethylene, polypropylene, polyurethane, soft polyvinyl chloride, polyfluoroethylene-propylene or the like is preferably adopted.

The piercing member 5 is inserted in the lumen 12 of the catheter 1. The piercing member 5 includes the piercing needle 51 provided at the distal end thereof, wire 52 whose distal end is connected to the proximal end of the piercing needle 51 and which extends beyond the catheter hub 11, and the wire hub 53 fixed to the proximal end of the wire 52. The piercing member 5 is slidably inserted in the lumen 12 of the catheter 1 and the distal end of the piercing needle 51 is disposed to extend beyond the distal end of the catheter 1. A distance d (refer to FIG. 2) between the distal end of the catheter 1 and an edge face of the piercing needle 51 is referred to as the "lie distance". A suitable lie distance is to be provided in order to pierce and insert the catheter 1 into a human body together with the piercing needle 51.

Figure 4:
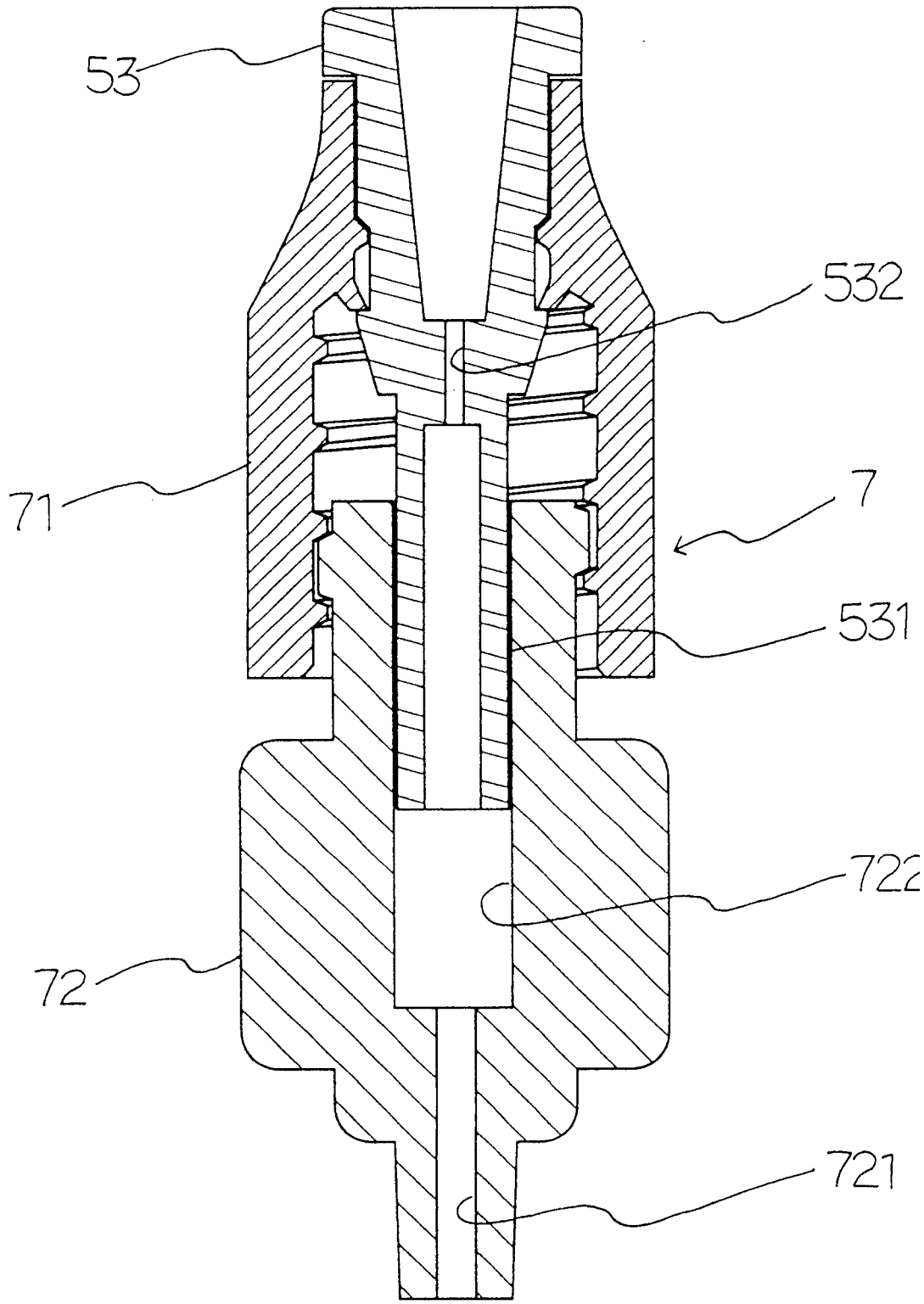
FIG. 4 is an enlarged longitudinal sectional view showing a portion including a wire hub of FIG. 1.

However, actually, it is the existing state that a suitable lie distance sometimes cannot be provided since the wire 52 may be twisted in the catheter 1 or a variation in fixing the wire 52 to the wire hub 53 is large. If the lie distance is not suitable, the piercing resistance is increased and significant pain is inflicted on a patient. To avoid such problems an adjusting means 7 for adjusting the direction of the edge face and the lie distance d may be preferably provided to the wire hub 53 of the catheter assembly according to the present invention as shown in FIG. 4. When the adjusting means 7 is provided, a distal end portion 531 shaped like a tube in which the wire 52 can be rot ably inserted is preferably provided on the wire hub 53. The adjusting means 7 is comprised of a female screw member 71 which is rotatably attached to the outer periphery of the wire hub 53 and a male screw member 72 which can be screwed into said female screw member 71. The male screw member 72 has a longitudinal bore 721 and a longitudinal bore 722. The wire 52 can be rotatably inserted in the bore 721 in the longitudinal direction. The bore 722 is larger than the hole 721 and the distal end portion 531 of the wire hub 53 can be inserted therein. By inserting the distal end portion 531 of the wire hub 53 in the bore 722, the male screw member 72 and the wire hub 53 can be rotated together. Incidentally, numeral 532 designates a hole for attaching the wire 52.

If adjusting means 7 is provided to the wire hub 53, when the male screw member 72 is rotated, the wire hub 53 having the distal end portion 531 thereof inserted in bore 722 of the male screw member 72, is rotated along therewith. Therefore, the direction of the edge face of the piercing needle 51 can be adjusted. Also, after adjusting the direction of the edge face, when the male screw member 72 is fixed by hand and the female screw member 71 is rotated, the wire hub 53 is moved forward or backward, and thus, a suitable lie distance can be selected.

Figure 5:
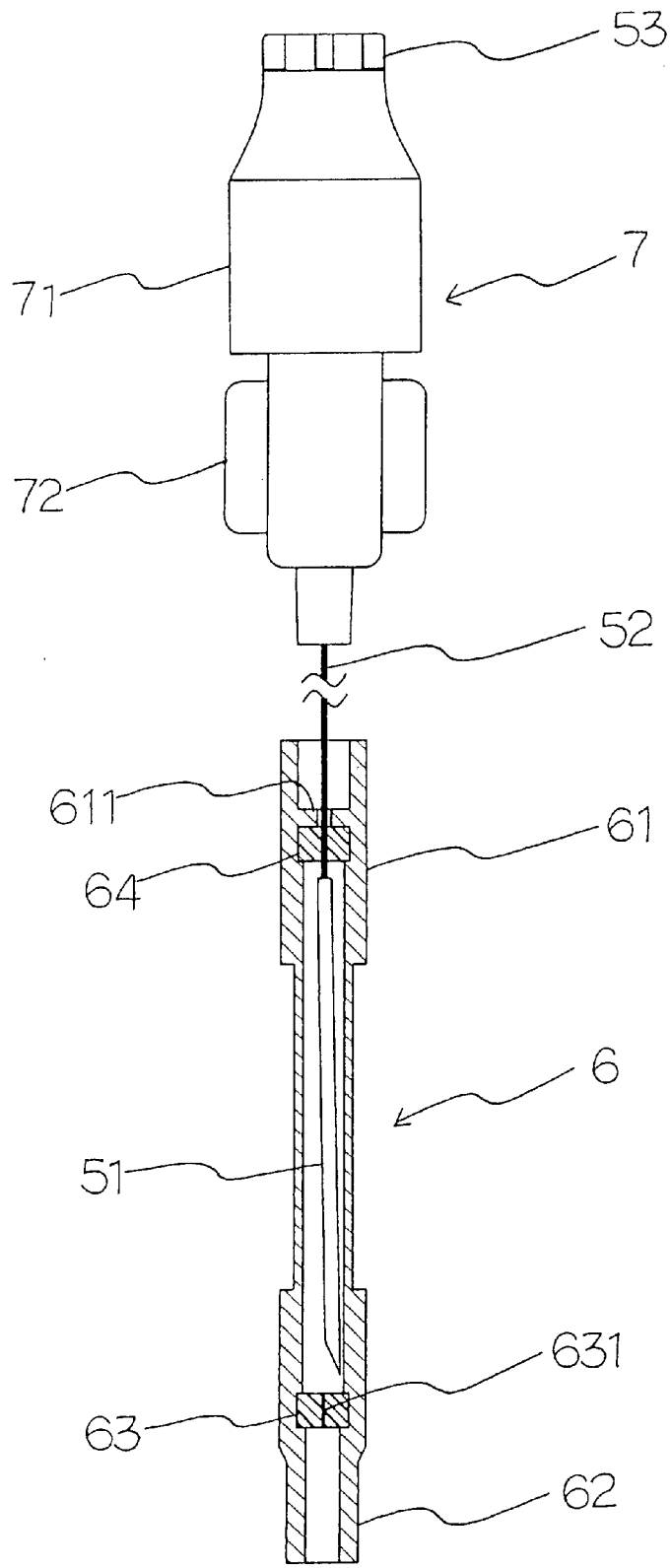
FIG. 5 is a partially sectioned plane view showing a state where a piercing needle is accommodated in a long accommodating tube of an embodiment of the invention as shown in FIG. 1.
Figure 6:
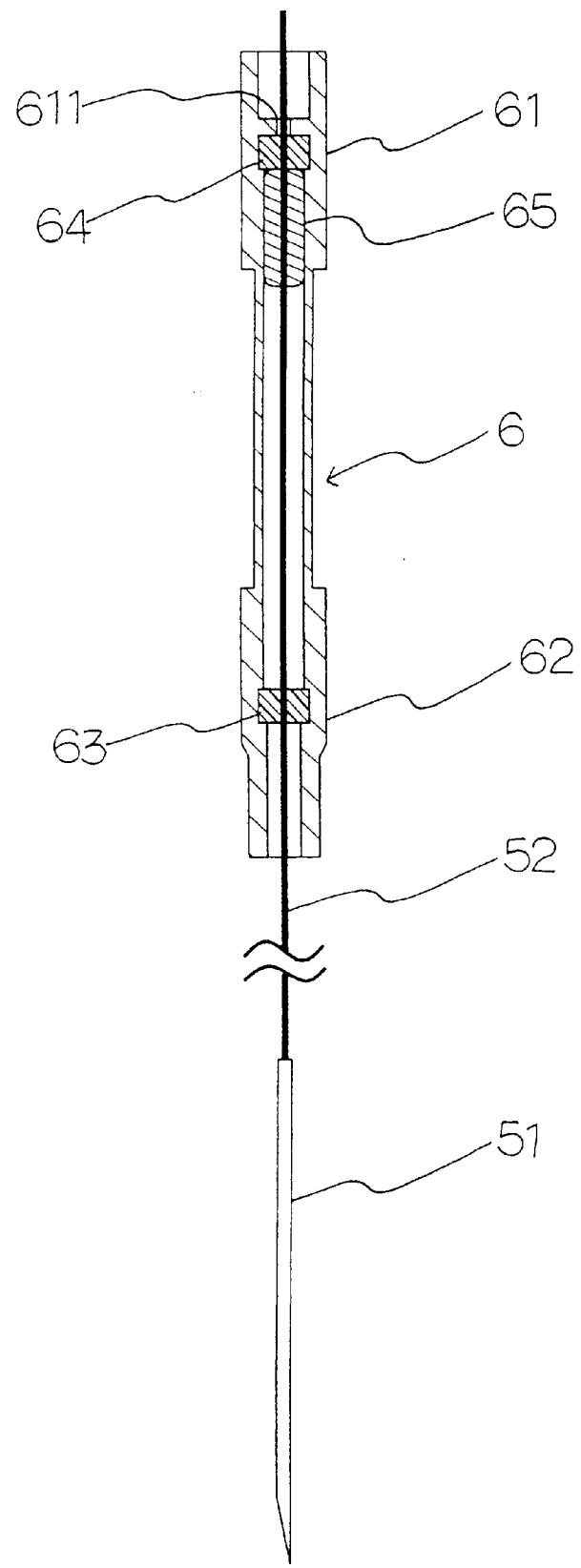
FIG. 6 is a partially sectioned plane view showing other embodiment of a long accommodating tube.

A catheter assembly of the present invention may be preferably provided with a long accommodating tube 6 coaxial with the wire 52 and between the catheter hub 11 and the wire hub 53 for accommodating a piercing member therein as illustrated in FIGS. 5 through 8. The long accommodating tube 6 shown in FIG. 5 is a tubular member having a proximal end portion 61 and a distal end portion 62. The proximal end portion 61 and the distal end portion 62 are detachably connected to the wire hub 53 and the catheter hub 11, respectively. The proximal end portion 61 has a narrow portion 611 through which the wire 52 can pass but the piercing needle 51 cannot pass. The distal end portion 62 is closed by a rubber plug 63 which is provided with a hole 631 (or a slit) through which the wire 62 and the piercing needle 51 can pass. The distance between the narrow portion 611 and the rubber plug 63 is larger than the length of the piercing needle 51. Incidentally, a similar rubber plug 64 may be provided contiguously to the narrow portion 611 of the proximal end portion 61 as necessary (as shown in FIG. 5). Further, as shown in FIG. 6, a wire disinfecting member 65 can be accommodated in the long accommodating tube 6 surrounding the wire 52 contiguously to the narrow portion 611 (or the rubber plug 64 if the rubber plug 64 is provided).

Figure 7:
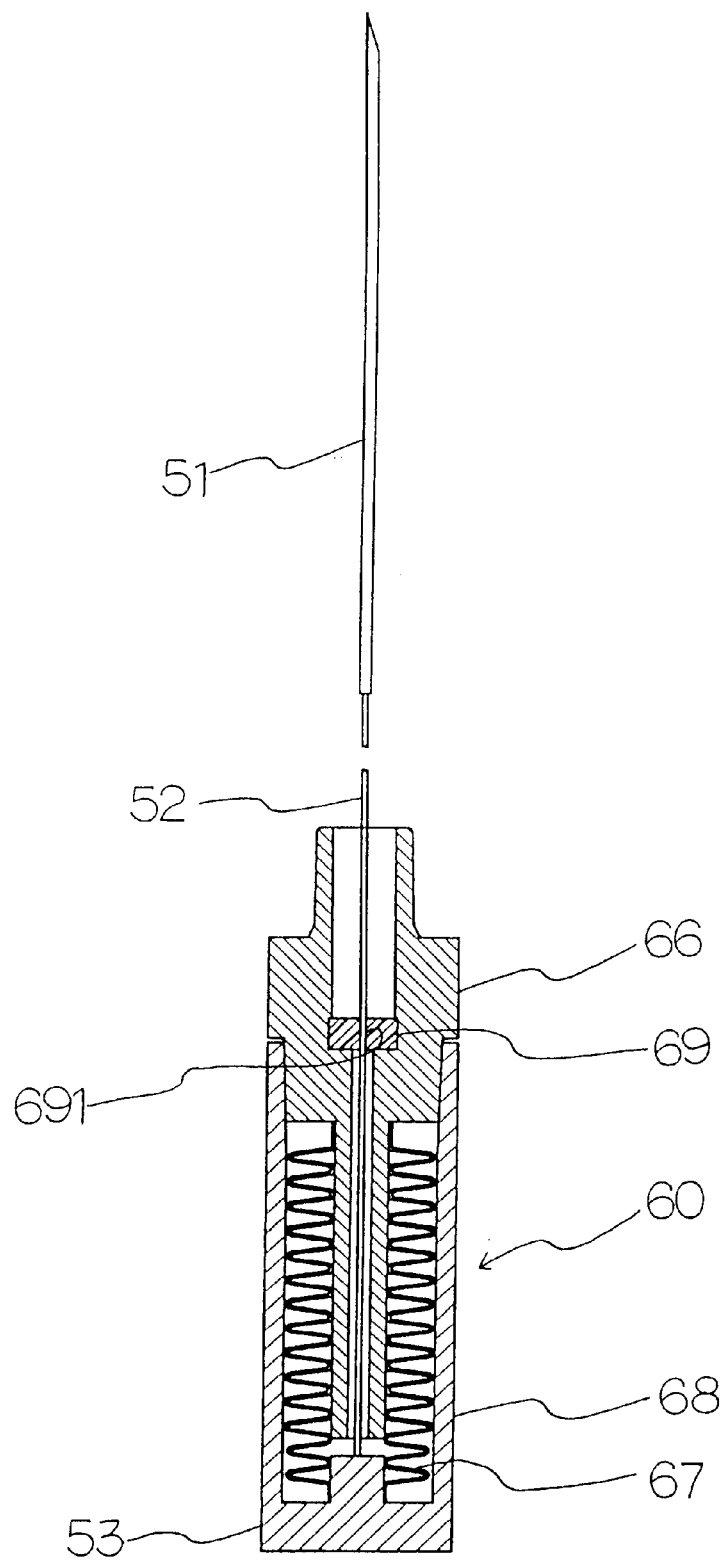
FIG. 7 is a sectional view showing still other embodiment of a long accommodating tube.
Figure 8:
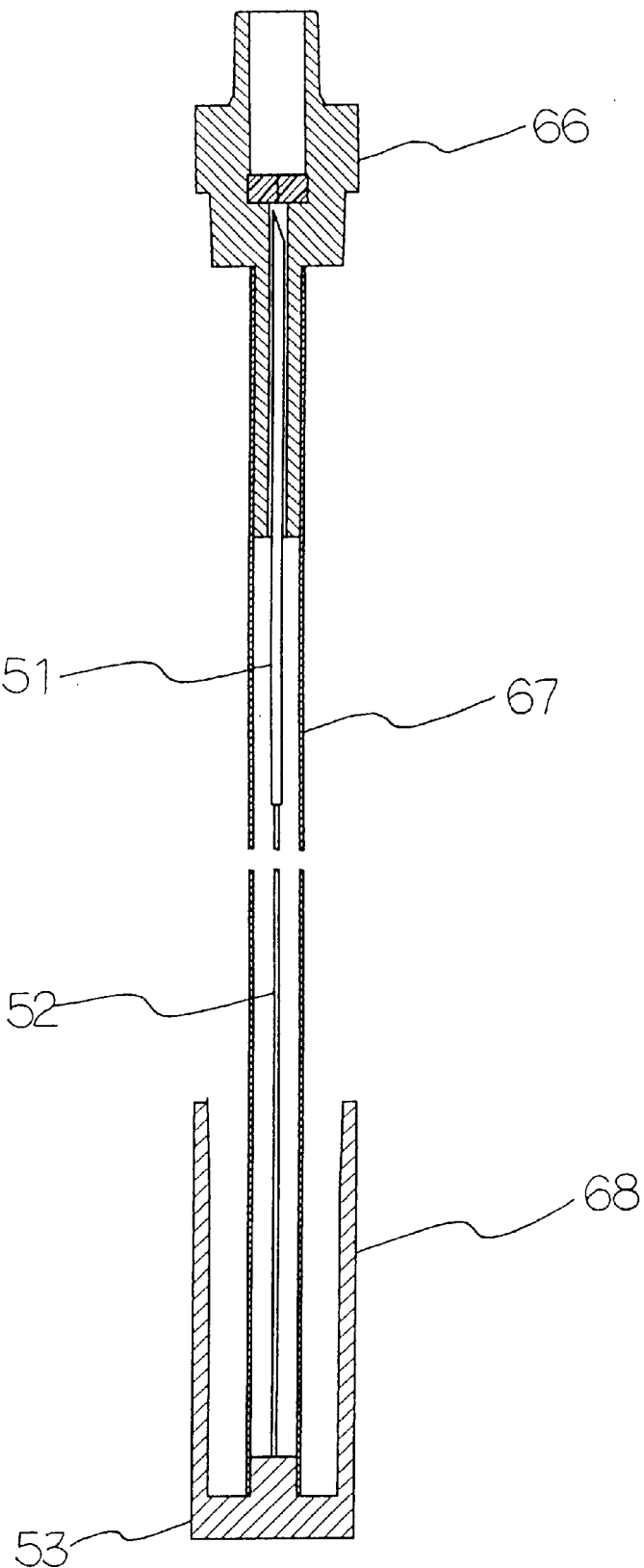
FIG. 8 is a view showing a state where a piercing member is accommodated in the long accommodating tube of FIG. 7.

The long accommodating tube may also have a structure which can be accommodated with the wire 52 as shown in FIGS. 7 and 8. A long accommodating tube 60 is comprised of a connection member 66 whose distal end is connectable to the catheter hub 11, a soft sleeve 67 whose distal end is connected to a proximal end of the connection member 66, and a sleeve protecting cylinder 68 capable of accommodating the sleeve 67 therein. The soft sleeve 67 is constructed of a film or a sheet made of synthetic resin such as polyethylene, polypropylene, polyvinyl chloride, polyester or the like. The proximal end of the sleeve 67 is connected to the wire hub 53 (or the adjusting means 7 if the wire hub 53 is provided with adjusting means 7). The long accommodating tube 60 can be connected to the catheter hub 11 and the wire hub 53 (or the adjusting means 7 if the wire hub 53 is provided with the adjusting means). The connection member 66 is provided with a rubber plug 69 which is formed with a hole 691 such that the piecing needle 51 cannot be retrogressed after passing thorough the hole 691. The length of the sleeve 67 is determined such that piecing needle 51 can pass through the rubber plug 69 when the sleeve 67 is extended. Incidentally, although the sleeve protecting cylinder 68 may be connectable to the connection member 66 and the wire hub 53 by fixing, screwing, fitting or the like, it is necessary that at least one of the connection member 66 and the wire hub 53 is detachable.

In respect of the long accommodating tube 60, as shown by FIG. 7, the sleeve 67 is accommodated in the sleeve protecting cylinder 68 in a state such that it is folded up in the longitudinal direction before accommodating the piercing member 5. After accommodating the piercing member 5, in the case of a structure where the sleeve protecting cylinder 68 is attached, for example, to the wire hub 53 as shown in FIG. 8, when the sleeve protecting cylinder 68 is detached from the connection member 66 by turning the wire hub 53 (or the sleeve protecting cylinder 68) and the wire hub 53 is pulled rearwardly, the sleeve 67 is extended and the piercing needle 51 and the wire 52 of the piercing member 5 are accommodated in the long accommodating tube 60. Accordingly, when the long accommodating tube 60 is adopted, the wire 52 is also accommodated therein and, therefore, safe operation is achieved even in the case where the wire 52 is contaminated by blood.

As is apparent from the above-described explanation, the following effects can be achieved by adopting the catheter assembly of the present invention.

(1) A tubular member is provided at the proximal end portion of the support channel of the wing member and, when the sheath is pushed along the tubular member, the sheath is stripped from the tubular member after separating the sheath from the catheter by the tubular member. Therefore, because exposure of the catheter in the stripping operation can be prevented, and the stripping resistance of the sheath does not directly act on the catheter and kinking or bending of the catheter caused by such stripping resistance does not occur, the catheter can be sanitarily and safely inserted into a desired position of a human body by pushing the catheter.

(2) The wire hub is provided with an adjusting means for adjusting the direction of the edge face and the lie distance, and because the direction of the edge face of the piercing needle can be adjusted or a pertinent lie distance can be selected, a variation caused in fabrication or in fixing the wire to the wire hub and an influence by twisting of the edge face can be adjusted. Thus, pain caused by the penetration force in piercing the needle into a patient can be alleviated.

(3) A long accommodating tube for accommodating the piercing member is provided between the catheter hub and the wire hub coaxially with the wire and a used piercing needle can be accommodated therein, and therefore, erroneous piercing accidents can be prevented.

(4) When the long accommodating tube is provided with a structure such that the wire can be accommodated, safe operation can be achieved even in the case where the wire is contaminated by blood.

What is claimed is:

1. A catheter assembly comprising:
   a catheter having a lumen extending from a proximal end to a distal end thereof and having a first catheter hub provided at the proximal end thereof;
   a wing member having a support channel for slidably accommodating and supporting the catheter therein;
   a tubular member fixed to a proximal end of the support channel of the wing member, said catheter being slidably inserted therein;
   a sheath having a slit or a weakened portion extending in a longitudinal direction from a distal end to a proximal end thereof, said sheath slidably covering the catheter and the tubular member and being fixed to said first catheter hub coaxially with the catheter; and
   a piercing member slidably inserted through the lumen of the catheter, said piercing member including a piercing needle provided at a distal end thereof, a wire having a distal end connected to a proximal end of the piercing needle and extending beyond said first catheter hub, and a second wire hub fixed to a proximal end of said wire, wherein a distal end of the piercing needle extends beyond the distal end of the catheter.

2. The catheter assembly according to claim 1, wherein a sheath stripping member is provided contiguously to the proximal end of the support channel and on a periphery of the tubular member, said sheath stripping member having an outer diameter thereof that is gradually increased in a direction of a distal end of said support channel, an outer diameter of a distal end of said sheath stripping member being larger than an inner diameter of the sheath.

3. The catheter assembly according to claim 1, wherein said second wire hub is provided with an adjusting means for adjusting a direction of an edge face and a lie distance of the piercing needle.

4. The catheter assembly according to claim 2, wherein said second wire hub is provided with an adjusting means for adjusting a direction of an edge face and a lie distance of the piercing needle.

5. The catheter assembly according to claim 1, wherein a long accommodating tube for accommodating the piercing member therein is provided between said first catheter hub and said second wire hub coaxially with the wire.

6. The catheter assembly according to claim 2, wherein a long accommodating tube for accommodating the piercing member therein is provided between said first catheter hub and said second wire hub coaxially with the wire.

7. The catheter assembly according to claim 3, wherein a long accommodating tube for accommodating the piercing member therein is provided between said first catheter hub and said second wire hub coaxially with the wire.

8. The catheter assembly according to claim 5, wherein the long accommodating tube comprises a connection member having a distal end detachably connected to said first catheter hub, an extendable soft sleeve having a distal end connected to a proximal end of the connection member, and a sleeve protecting cylinder capable of accommodating said sleeve therein; and
   wherein a proximal end of said sleeve is connected to said wire hub and said long accommodating tube is detachably connected to said first catheter hub and said second wire hub.

9. The catheter assembly according to claim 6, wherein the long accommodating tube comprises a connection member having a distal end detachably connected to said first catheter hub, an extendable soft sleeve having a distal end connected to a proximal end of the connection member, and a sleeve protecting cylinder capable of accommodating said sleeve therein; and
   wherein a proximal end of said sleeve is connected to said wire hub and said long accommodating tube is detachably connected to said first catheter hub and said second wire hub.

10. The catheter assembly according to claim 7, wherein the long accommodating tube comprises a connection member having a distal end detachably connected to said first catheter hub, an extendable soft sleeve having a distal end connected to a proximal end of the connection member, and a sleeve protecting cylinder capable of accommodating said sleeve therein; and
    wherein a proximal end of said sleeve is connected to said wire hub and said long accommodating tube is detachably connected to said first catheter hub and said second wire hub.

11. The catheter assembly according to claim 5, wherein the long accommodating tube includes a wire disinfecting member provided around the wire.

12. The catheter assembly according to claim 6, wherein the long accommodating tube includes a wire disinfecting member provided around the wire.

13. The catheter assembly according to claim 7, wherein the long accommodating tube includes a wire disinfecting member provided around the wire.

* * * * *